(12) United States Patent
Teague (10) Patent No.: US 7,828,746 B2
(45) Date of Patent: Nov. 9, 2010

(54) OBTAINING A TISSUE SAMPLE (75) Inventor: James A. Teague, Spencer, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 0 days.

(21) Appl. No.: 12/323,979

(22) Filed: Nov. 26, 2008

(65) Prior Publication Data

US 2009/0131826 A1 May 21, 2009

Related U.S. Application Data (62) Division of application No. 11/362,894, filed on Feb. 24, 2006, now Pat. No. 7,473,232.

(51) Int. Cl.
A61B 10/00 (2006.01)
(52) U.S. Cl. .............. 600/566; 600/562; 600/564; 600/565; 600/567; 600/570; 600/571
(58) Field of Classification Search ............... 600/562, 600/564–567, 570, 571
See application file for complete search history.

(56) References Cited

U.S. PATENT DOCUMENTS

| 4,434,797 | A |   | 3/1984  | Silander            |
|-----------|---|---|---------|---------------------|
| 4,590,938 | A |   | 5/1986  | Segura et al.       |
| 4,655,771 | A |   | 4/1987  | Wallsten            |
| 4,762,128 | A |   | 8/1988  | Rosenbluth          |
| 4,873,991 | A | * | 10/1989 | Skinner ..... 600/567 |
| 4,884,572 | A |   | 12/1989 | Bays et al.         |
| 4,903,709 | A | * | 2/1990  | Skinner ..... 600/567 |
| 4,911,687 | A |   | 3/1990  | Stewart et al.      |
| 4,946,449 | A |   | 8/1990  | Davis, Jr.          |
| 4,955,859 | A |   | 9/1990  | Zilber              |
| 4,958,625 | A |   | 9/1990  | Bates et al.        |
| 4,978,341 | A |   | 12/1990 | Nierderhauser       |
| 4,994,066 | A |   | 2/1991  | Voss                |
| 5,027,827 | A |   | 7/1991  | Cody et al.         |
| 5,057,114 | A |   | 10/1991 | Wittich et al.      |
| 5,064,428 | A |   | 11/1991 | Cope et al.         |
| 5,123,917 | A |   | 6/1992  | Lee                 |
| 5,127,419 | A | * | 7/1992  | Kaldany ..... 600/567 |
| 5,176,688 | A |   | 1/1993  | Narayan et al.      |
| 5,195,533 | A |   | 3/1993  | Chin et al.         |
| 5,246,445 | A |   | 9/1993  | Yachia et al.       |
| 5,267,572 | A |   | 12/1993 | Bucalo              |
| 5,269,802 | A |   | 12/1993 | Garber              |
| 5,320,110 | A | * | 6/1994  | Wang ..... 600/566  |
| 5,356,423 | A |   | 10/1994 | Tihon et al.        |
| 5,368,045 | A |   | 11/1994 | Clement et al.      |
| 5,374,273 | A |   | 12/1994 | Nakao et al.        |
| 5,391,196 | A |   | 2/1995  | Devonec             |
| 5,415,182 | A |   | 5/1995  | Chin et al.         |
| 5,417,691 | A |   | 5/1995  | Hayhurst            |
| 5,449,001 | A | * | 9/1995  | Terwilliger ..... 600/567 |

(Continued)

FOREIGN PATENT DOCUMENTS

DE 197 13 280 10/1998

(Continued)

OTHER PUBLICATIONS

Stoeckel et al., "Superelastic Ni-Ti Wire", *Wire Journal International*, Mar. 1991, pp. 45-50.

(Continued)

*Primary Examiner*—Max Hindenburg
*Assistant Examiner*—Sean P Dougherty
(74) *Attorney, Agent, or Firm*—Brown Rudnick LLP (57) ABSTRACT A device with a sampling portion configured to engage, sever, and remove tissue from a body can be used to obtain one or more tissue samples from the body. The device can be used to obtain multiple tissue samples simultaneously.

13 Claims, 5 Drawing Sheets

U.S. PATENT DOCUMENTS

| | | | |
|---|---|---|---|
| 5,456,265 A * | 10/1995 | Yim | 600/569 |
| 5,458,112 A | 10/1995 | Weaver | |
| 5,471,992 A | 12/1995 | Banik et al. | |
| 5,511,556 A * | 4/1996 | DeSantis | 600/567 |
| 5,514,176 A | 5/1996 | Bosley, Jr. | |
| 5,518,498 A | 5/1996 | Lindenberg et al. | |
| 5,562,102 A | 10/1996 | Taylor | |
| 5,573,008 A | 11/1996 | Robinson et al. | |
| 5,601,585 A | 2/1997 | Banik et al. | |
| 5,601,591 A | 2/1997 | Edwards et al. | |
| 5,660,186 A * | 8/1997 | Bachir | 600/562 |
| 5,667,486 A | 9/1997 | Mikulich et al. | |
| 5,715,832 A | 2/1998 | Koblish et al. | |
| 5,718,237 A | 2/1998 | Haaga | |
| 5,749,889 A | 5/1998 | Bacich et al. | |
| 5,766,209 A | 6/1998 | Devonec | |
| 5,782,855 A | 7/1998 | Lau et al. | |
| 5,810,744 A | 9/1998 | Chu et al. | |
| 5,840,044 A | 11/1998 | Dassa et al. | |
| 5,873,886 A * | 2/1999 | Larsen et al. | 606/180 |
| 5,916,145 A | 6/1999 | Chu et al. | |
| 5,928,163 A | 7/1999 | Roberts et al. | |
| 5,928,217 A | 7/1999 | Mikus et al. | |
| 5,957,863 A | 9/1999 | Koblish et al. | |
| 5,957,932 A | 9/1999 | Bates et al. | |
| 5,964,771 A | 10/1999 | Beyar et al. | |
| 5,968,052 A | 10/1999 | Sullivan, III et al. | |
| 5,971,940 A | 10/1999 | Baker et al. | |
| 5,989,196 A | 11/1999 | Chu et al. | |
| 5,989,266 A | 11/1999 | Foster | |
| 6,019,744 A | 2/2000 | Altdorf et al. | |
| 6,033,413 A | 3/2000 | Mikus et al. | |
| 6,059,793 A | 5/2000 | Pagedas | |
| 6,083,220 A | 7/2000 | Guglielmi et al. | |
| 6,096,053 A | 8/2000 | Bates | |
| 6,099,534 A | 8/2000 | Bates et al. | |
| 6,142,957 A | 11/2000 | Diamond et al. | |
| 6,146,415 A | 11/2000 | Fitz | |
| 6,152,932 A | 11/2000 | Ternstrom | |
| 6,159,220 A | 12/2000 | Gobron et al. | |
| 6,162,231 A | 12/2000 | Mikus et al. | |
| 6,168,617 B1 | 1/2001 | Blaeser et al. | |
| 6,187,017 B1 | 2/2001 | Gregory, Jr. | |
| 6,224,612 B1 | 5/2001 | Bates et al. | |
| 6,261,242 B1 | 7/2001 | Roberts et al. | |
| 6,264,618 B1 | 7/2001 | Landi | |
| 6,264,664 B1 | 7/2001 | Avellanet | |
| 6,270,523 B1 | 8/2001 | Herweck et al. | |
| 6,280,451 B1 | 8/2001 | Bates et al. | |
| 6,293,909 B1 | 9/2001 | Chu et al. | |
| 6,296,608 B1 | 10/2001 | Daniels et al. | |
| 6,302,895 B1 | 10/2001 | Gobron et al. | |
| 6,319,262 B1 | 11/2001 | Bates et al. | |
| 6,331,165 B1 | 12/2001 | Turturro et al. | |
| 6,361,504 B1 * | 3/2002 | Shin | 600/562 |
| 6,364,840 B1 | 4/2002 | Crowley | |
| 6,419,681 B1 * | 7/2002 | Vargas et al. | 606/153 |
| 6,425,887 B1 * | 7/2002 | McGuckin et al. | 604/272 |
| 6,514,215 B1 * | 2/2003 | Ouchi | 600/564 |
| 6,520,968 B2 | 2/2003 | Bates et al. | |
| 6,537,288 B2 * | 3/2003 | Vargas et al. | 606/153 |
| 6,569,150 B2 | 5/2003 | Teague et al. | |
| 6,585,655 B2 | 7/2003 | Crowley | |
| 6,673,080 B2 | 1/2004 | Reynolds et al. | |
| 6,743,185 B2 | 6/2004 | Weber et al. | |
| 6,858,014 B2 | 2/2005 | Damarati | |
| 6,890,309 B2 | 5/2005 | Fisher | |
| 6,926,676 B2 | 8/2005 | Turturro et al. | |
| 6,942,673 B2 | 9/2005 | Bates et al. | |
| 6,958,044 B2 * | 10/2005 | Burbank et al. | 600/564 |
| 6,969,299 B1 | 11/2005 | Papetti | |
| 6,986,748 B2 | 1/2006 | McAlister et al. | |
| 6,994,712 B1 | 2/2006 | Fisher et al. | |
| 7,001,341 B2 | 2/2006 | Gellman et al. | |
| 7,048,751 B2 * | 5/2006 | Vargas et al. | 606/153 |
| 7,226,424 B2 * | 6/2007 | Ritchart et al. | 600/566 |
| 7,276,032 B2 * | 10/2007 | Hibner | 600/564 |
| 2002/0010459 A1 | 1/2002 | Whittier et al. | |
| 2002/0026203 A1 | 2/2002 | Bates et al. | |
| 2002/0029006 A1 | 3/2002 | Turturro et al. | |
| 2002/0038119 A1 | 3/2002 | Weber et al. | |
| 2002/0052564 A1 | 5/2002 | Burbank et al. | |
| 2002/0188201 A1 | 12/2002 | Crowley | |
| 2003/0088254 A1 | 5/2003 | Gregory, Jr. et al. | |
| 2003/0093007 A1 | 5/2003 | Wood | |
| 2003/0093067 A1 | 5/2003 | Panescu | |
| 2003/0097146 A1 | 5/2003 | Montalvo et al. | |
| 2003/0135233 A1 | 7/2003 | Bates et al. | |
| 2003/0191413 A1 | 10/2003 | Damarati | |
| 2003/0199986 A1 | 10/2003 | McWeeney et al. | |
| 2003/0236536 A1 | 12/2003 | Grigoryants et al. | |
| 2004/0064067 A1 | 4/2004 | Ward | |
| 2004/0116941 A1 | 6/2004 | Reynolds et al. | |
| 2004/0122445 A1 | 6/2004 | Butler et al. | |
| 2004/0138677 A1 | 7/2004 | Little et al. | |
| 2004/0138733 A1 | 7/2004 | Weber et al. | |
| 2004/0181169 A1 | 9/2004 | Diamond et al. | |
| 2004/0181243 A1 | 9/2004 | Chu et al. | |
| 2005/0033354 A1 | 2/2005 | Montalvo et al. | |
| 2005/0043758 A1 | 2/2005 | Golden et al. | |
| 2005/0080435 A1 * | 4/2005 | Smith et al. | 606/151 |
| 2005/0090765 A1 | 4/2005 | Fisher | |
| 2005/0113854 A1 | 5/2005 | Uckele | |
| 2005/0113867 A1 | 5/2005 | Anderhub et al. | |
| 2005/0124912 A1 | 6/2005 | Griego et al. | |
| 2005/0124913 A1 | 6/2005 | Damarati | |
| 2005/0165329 A1 | 7/2005 | Taylor et al. | |
| 2005/0216029 A1 | 9/2005 | Gingrich et al. | |
| 2005/0234443 A1 | 10/2005 | Rioux et al. | |
| 2005/0240218 A1 | 10/2005 | Freed et al. | |
| 2006/0009711 A1 | 1/2006 | Gingrich et al. | |
| 2006/0009786 A1 | 1/2006 | Bates et al. | |
| 2006/0030753 A1 | 2/2006 | Boutillette et al. | |
| 2006/0036182 A1 | 2/2006 | Daniels et al. | |
| 2006/0036211 A1 * | 2/2006 | Solsberg et al. | 604/48 |
| 2006/0058703 A1 * | 3/2006 | Huenerbein | 600/567 |
| 2006/0129101 A1 * | 6/2006 | McGuckin, Jr. | 604/164.01 |
| 2006/0167377 A1 * | 7/2006 | Ritchart et al. | 600/566 |
| 2007/0016101 A1 * | 1/2007 | Feldman et al. | 600/567 |
| 2007/0106176 A1 * | 5/2007 | Mark et al. | 600/566 |
| 2007/0156064 A1 * | 7/2007 | Ritchart et al. | 600/564 |
| 2008/0154151 A1 * | 6/2008 | Ritchart et al. | 600/566 |
| 2009/0023982 A1 * | 1/2009 | Karram | 600/37 |
| 2009/0143698 A1 * | 6/2009 | Janssens | 600/566 |
| 2009/0177161 A1 * | 7/2009 | McGuckin et al. | 604/164.11 |

FOREIGN PATENT DOCUMENTS

| | | |
|---|---|---|
| EP | 1 110 561 | 6/2001 |
| FR | 2 767 673 | 3/1999 |
| SR | 1 412 774 | 7/1988 |
| WO | WO-93/15671 | 8/1993 |
| WO | WO-99/48429 | 12/1999 |
| WO | WO-00/44308 | 8/2000 |
| WO | WO-00/71036 | 11/2000 |
| WO | WO-01/10290 | 2/2001 |

OTHER PUBLICATIONS

International Search Report dated Sep. 29, 2008, issued in international application No. PCT/US06/48977.

* cited by examiner

OBTAINING A TISSUE SAMPLE

CROSS-REFERENCE TO RELATED APPLICATION

This application is a divisional application of U.S. patent application Ser. No. 11/362,894 filed on Feb. 24, 2006, now U.S. Pat. No. 7,473,232, the entirety of which is incorporated herein by reference.

TECHNICAL FIELD

The present invention generally relates to obtaining samples of tissue.

BACKGROUND INFORMATION

Biopsy is a medical diagnostic test used to determine the structure and composition of tissues or cells. In particular, cells or living tissues are sampled from an organ or other body part and are examined under microscope. For example, if an abnormality is found, a biopsy can be performed to determine the exact nature of the suspected abnormality. For example, a physician may perform a biopsy as part of cancer diagnosis in order to determine whether an area of concern is malignant (cancerous) or benign (not cancerous).

Biopsies can be performed on a number of organs, tissues, and body sites. A bone biopsy may be performed if the patient experiences bone pain and/or demonstrates other indicators of bone cancer. A bone marrow biopsy may be performed for individuals with abnormal blood counts. A breast biopsy is performed to confirm if a lesion is benign or malignant. A cervical biopsy is often performed to diagnose cervical diseases such as cervical cancer. Joint biopsy can be used to diagnose gout, pseudogout, bacterial infections, lupus, rheumatoid arthritis or Reiter's disease. Kidney biopsy can be performed to diagnose a long list of disorders including glomerulonrphritis, systemic lupus erythematosus, Wilms' tumour and renal cell cancer, and may be performed if blood is found in the urine, if there is excessive protein in the urine, and in cases of impaired kidney function which causes excessive waste products in the blood. Liver biopsy may help identify liver disorders and diagnose abnormalities as benign or malignant. Lymph node biopsy can be performed to look for diseases such as chronic lymphatic leukemia, Hodgkin's disease, infectious mononucleosis, and rheumatoid arthritis, and can be used to determine the stage of cancer by checking whether the cancer has spread from the primary location into the lymphatic system. Lung biopsy is performed to confirm lung diseases such as cancer and to diagnose abnormalities. Pleural biopsy is sampling of the pleura (the sac that covers the lungs) and may be performed to differentiate between malignant and non-malignant disease and to diagnose various diseases of the pleura (e.g. viral, fungal, parasitic, or collagen vascular disease). Prostate biopsy can be used to diagnose prostate cancer or to determine the cause of prostate enlargement or elevated serum prostate markers (e.g. PSA—prostate specific antigen). Small intestine biopsy is often performed to determine what may be causing diarrhea or poor absorption in the intestine. Skin biopsy is used to test for malignant cancer and to diagnose various skin infections. Synovial biopsy is used to sample synovial tissue from the surface of a joint. Thyroid and parathyroid biopsy maybe used to diagnose people with thyroid enlargement or nodules, breathing and swallowing difficulties, vocal chord paralysis and other problems such as unexplainable weight loss. Thyroid biopsy may also be used to diagnose Hashimoto's disease, hyperthyroidism, and nontoxic nodular goiter. A biopsy may also be performed to sample the following organs to test for cancer and other diseases: adrenal gland, biliary tract, bladder, carpal tunnel, colon, endometrium, gingiva (gums), heart, muscle, nerve, salivary gland, small bowel, mouth, nasal mucosa, rectum, testicle, throat, and tongue.

The type of biopsy procedure used to obtain a required tissue sample depends on a variety of factors including: the tissue or body part to be sampled, the location, size, shape and other characteristics of the abnormality, the number of abnormalities, and patient preference. Aspiration or FNA (fine needle aspiration) biopsy is a percutaneous biopsy performed using fine gauge needle (22 or 25 gauge) attached to a syringe. Cone biopsy removes a generally cylindrical or cone shaped piece of tissue using either the LEEP method (loop electrosurgical excision procedure) wherein tissue is removed using an electrically heated wire, or a method using a surgical scalpel or laser to remove the tissue. Core needle biopsy is a percutaneous procedure performed by inserting a small hollow needle through the skin and into the abnormality such that a sample or core is removed as the needle is advanced through the cell layers. A suction or vacuum assisted core biopsy is generally a core biopsy using vacuum assistance to pull the sample from the collection site. Endoscopic biopsy is a biopsy performed through an endoscope (a fiber optic cable for viewing inside the body), wherein samples may be removed using forceps attached to a cable that runs inside the endoscope. A punch biopsy uses a sharp, hollow instrument (like a cookie cutter) to remove a cylindrical piece of skin, for example, from a mole. A surface biopsy involves sampling or scraping off superficial levels of skin and is often performed by dermatologists to remove a small piece of skin to test for carcinoma. Surgical/excisional biopsy is generally performed as an open procedure and can be either excisional (removal of an entire lesion) or incisional (removal of a piece of a lesion).

Fine needle biopsies, unlike surgical biopsies, cannot remove the entire lesion and misdiagnosis can occur. Core needle biopsy removes more tissue than fine needle biopsy and, thus, may provide a more accurate analysis and diagnosis. However, this procedure is not accurate in patients with very small or hard lumps. While surgical biopsies remove more tissues and, thus, less prone to misdiagnosis, these procedures are significantly more expensive than needle biopsies, require more time for recuperation, require sutures, can leave a disfiguring scar, require anesthesia, carry a small risk of mortality, and can result in bleeding, infection and wound healing problems.

Brush biopsy or cytology is a type of sampling procedure wherein a brush having stiff bristles is inserted to the site and sample is collected as the bristles of the brush scrape or rub against the collection site. This method has been reported to obtain a complete transepithelial biopsy specimen from each of the three layers of the lesion (the basal, intermediate, and superficial layers). Such procedures find particular use in connection with many epithelial cancers and can be used to take rectal, cervical, and bladder samples. However, with such methods, only tiny pieces of tissue are obtained, and the brush must be removed from the site, the sample collected from the brush, and the brush reinserted to the site multiple times to collect an adequate sample for analysis.

SUMMARY OF THE INVENTION

The invention generally relates to obtaining tissue samples. Embodiments of devices and methods according to the invention can obtain multiple tissue samples simultaneously. Such devices and methods can be used for sampling tissues within a body passageway, such as the urethra or esophagus of a human or other mammal, and in other locations within the body, for example, for sampling tissues of organs. The devices and methods can involve the use of an endoscope or not. Because multiple tissue samples can be obtained simultaneously, it is not necessary to remove and reinsert the device to obtain more than one sample.

In one aspect, the invention generally relates to a device for obtaining at least one tissue sample from a site within a body of a patient. The device comprises an elongated member defining an interior passage and including a tissue sampling portion. The tissue sampling portion comprises a plurality of barbs for severing and removing a plurality of tissue samples from the site. The tissue sampling portion defines a plurality of openings for receiving the tissue samples. The openings are in communication with the interior passage. The tissue sampling portion is movable at the site to engage, sever, and remove the plurality of tissue samples from the site.

Embodiments according to this aspect of the invention can include the following features. The device can include, or be in connection with, an aspiration mechanism. The aspiration mechanism can be in connection with the elongated member for aspirating tissue from the openings and through the interior passage. The device can include a coaxial sheath, wherein the tissue sampling portion is slidably disposable between a housed position with the plurality of barbs disposed inside the sheath and a deployed position with the plurality of barbs disposed outside of the sheath. The plurality of barbs can extend out from the elongated member when the tissue sampling portion is in the deployed position, and the plurality of barbs can be pressed down toward the plurality of openings when the tissue sampling portion is in the housed position. The sampling portion can contain one or more barbs located at a first cross section of the sampling portion, can further contain one or more barbs located at a second cross section of the sampling portion, can further contain one or more barbs located at a third cross section of the sampling portion, and can further contain one or more barbs located at a fourth cross section of the sampling portion. One or more of the first, second, third, and fourth cross sections can comprises four equidistantly spaced barbs. In an embodiment, the sampling portion can have a length of approximately 10-20 mm. The elongated member can have a length of approximately 5-150 cm. The elongated member and sampling portion can be fabricated of a material selected from surgical grade stainless steel, anodized aluminum, Nitinol™ (an alloy of nickel and titanium), and polymeric materials and composites. At least a portion of the elongated member can be flexible. A handle can be located at the proximal end of elongated member.

The distal end of the elongated member can be sharpened for insertion of the elongated member into and through the site and/or into and through the skin. The distal end of the coaxial sheath can be sharpened for insertion of the sheath into the site and/or into and through the skin.

In another aspect, the invention generally relates to a method of obtaining a plurality of tissue samples from a site within a body of a patient. A device for obtaining the plurality of tissue samples is advanced to the site. The device comprises an elongated member including a proximal end, a distal end, and a plurality of barbs at the distal end. The site is contacted with at least two of the barbs, and the at least two barbs sever and remove the plurality of tissue samples. The device is subsequently withdrawn from the site.

Embodiments according to this aspect of the invention can include the following features. The elongated member can define an interior passage and a plurality of openings for receiving the plurality of tissue samples and being in communication with the interior passage. The method can further comprise, after severing and removing the plurality of tissue samples from the site, allowing the plurality of tissue samples to enter the interior passage through the openings. Aspiration can be provided through the elongated member to pull the plurality of tissue samples through the elongated member from the site. The device can further comprises a coaxial sheath in which the elongated member is slidably disposable between a housed position with the plurality of barbs disposed inside the sheath and a deployed position with the plurality of barbs disposed outside of the sheath. The method can further comprise disposing the elongated member in a housed position prior to advancing the device to the site, and, after the device is advanced to the site, disposing the elongated member in a deployed position. After severing and removing the plurality of tissue samples from the site, the elongated member can be disposed in a housed position. After disposing the elongated member in a housed position, aspiration can be provided through the elongated member to pull the tissue through the elongated member from the site. After providing aspiration through the elongated member, the elongated member can again be disposed in a deployed position, and the site contacted with at least two of the barbs so as to sever and remove a plurality of tissue samples from the site.

In another aspect, the invention generally relates to a method of forming a device for obtaining a plurality of tissue samples from a site within a body of a patient. According to the method, a plurality of portions of an elongated member are skived to form a plurality of barbs. Chemical etching can be used to sharpen the plurality of barbs.

Other aspects and advantages of the invention will become apparent from the following description, taken in conjunction with the accompanying drawings, illustrating the principles of the invention by way of example only.

BRIEF DESCRIPTION OF THE DRAWINGS

The foregoing and other objects, features, and advantages of the present invention, as well as the invention itself, will be more fully understood from the following description of various embodiments, when read together with the accompanying drawings.

DESCRIPTION

Embodiments of devices and methods according to the invention can be used to obtain multiple tissue samples simultaneously. The obtained samples can then be subjected to biopsy analysis. Such devices and methods can be used to collect samples along the walls of various body conduits or passageways (e.g., gastrointestinal tract, bronchial tract, urinary tract, colon, etc.) and at any location within the body of a human or other mammal where it is desirable to obtain tissue samples (e.g., from various organs such as lung, kidney, and liver). The devices and methods are suitable for use in obtaining biopsies from, but not limited to, bone, bone marrow, cervix, joints, kidney, liver, lymph node, lung, pleura, prostate, small intestine, skin, synovial, thyroid, parathyroid, adrenal gland, biliary tract, bladder, carpal tunnel, endometrium, gingiva (gums), heart, muscle, nerves, salivary gland, small bowel, mouth, nasal mucosa, testicle, tongue, throat, rectum, and colon. Further, the devices and methods are suitable for use in obtaining endoscopic biopsies (e.g., gastroscopy and colonoscopy). Thus, the disclosure to follow should be construed as illustrative rather than in a limiting sense. Further, while certain dimensions are provided, it is noted that such dimensions are based on the anatomy of an average adult male, and would be suitably scaled as required, for example, for children and women.

Figure 1A:
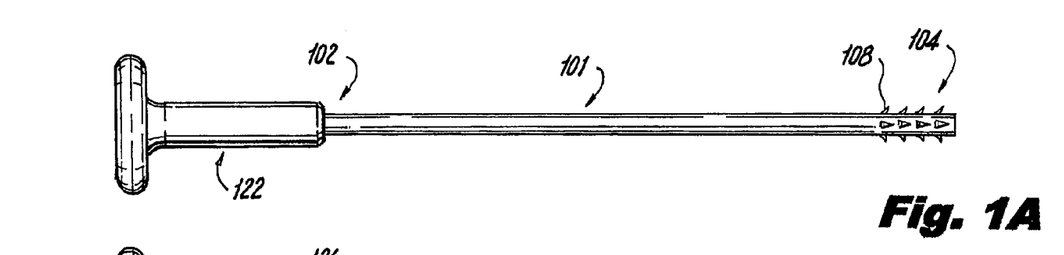
FIG. 1A shows a side view of one embodiment of the tissue sampling device.
Figures 1B, 1C, 1D:
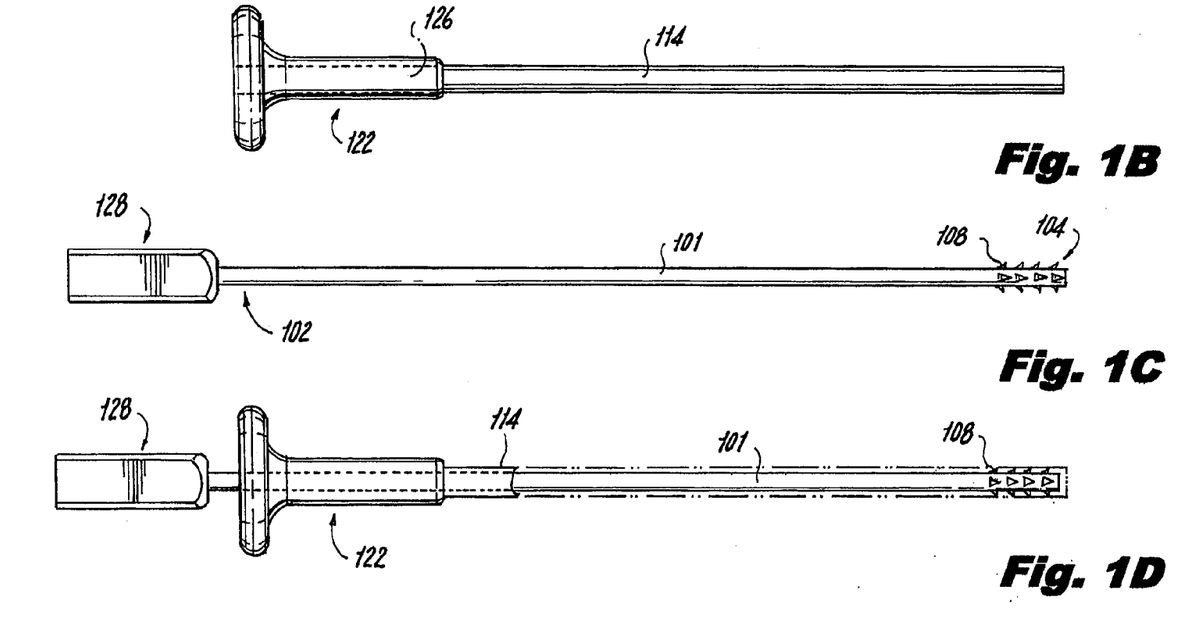
FIG. 1B shows a side view of a coaxial sheath having a hand piece.
FIG. 1C shows a side view of an elongated member having barbs at a distal end.
FIG. 1D shows a side view the elongated member and barbs of FIG. 1C housed within the coaxial sheath of FIG. 1B.

FIGS. 1A and 1B illustrate one embodiment of a tissue sampling device according to the invention. The tissue sampling device is generally configured to sever and remove one or more tissue samples from the body. In some embodiments, the tissue sampling device severs and removes a plurality of tissue samples from the body without being withdrawn from the body.

As shown in FIGS. 1A, 1C, 1D, 2A and 2B, the tissue sampling device includes an elongated member 101 having a proximal end 102, a distal end 104. The elongated member has an outer surface 106, as shown in FIGS. 2C, 3C, and 3D. In some embodiments, the device can include a hand piece 122. The hand piece 122 may be adapted to assist a user in securely gripping and manipulating the device and, for example, may include a rubber coating, grooves or similar finger grip configuration (e.g., surface preparations or artifacts), and the like.

The elongated member 101 can be tubular and hollow, as shown in the figures, with a generally circular cross-section. The elongated member 101 can also be provided in other geometric shapes. For example, the elongated member 101 can be solid. The elongated member 101 can also be solid with one or more channels or lumen (not shown) running along the length and/or width of the elongated member 101. The elongated member 101 can also have square, rectangular, triangular, or other geometrical cross-sectional shapes. Thus, while described and shown in the figures as an elongated hollow tubular member, the elongated member 101 is not limited as such.

A plurality of barbs 108 are disposed along at least a portion of the outer surface 106. Any number of barbs 108 can be used. To provide for the removal of multiple or adequate tissue sampling from the body, at least two barbs extend from the outer surface 106. The barbs 108 are configured so as to extend beyond the outer surface 106 such that, as the elongated member 101 is passed along or within a biopsy collection site, the barbs 108 engage, sever, and remove tissue from the tissue sampling site. The barbs 108 can be disposed anywhere along the length of the elongated member 101 and are positioned so as to provide tissue sampling as that portion of the elongated member 101 is placed in contact with the tissue sampling site. In one embodiment, for example, as shown in FIGS. 1A, 1B, 2A-C, 3A-C, and 4A-5B barbs 108 are located at the distal end 104 of the elongated member 101.

In one embodiment, shown in FIGS. 1A-3C, the barbs 108 can extend in a generally outwards and distal direction in relation to the outer surface 106. In this embodiment, the barbs 108 could engage, sever, and remove tissue as the device is moved in a distal (or forward) direction along or within a biopsy collection site. In another embodiment, shown in FIGS. 4A-B, the barbs 108 can extend in a generally outwards and proximal direction in relation to the outer surface 106. In this embodiment, the barbs 108 could engage, sever, and remove tissue as the device is moved in a proximal (or backward) direction along or within a biopsy collection site. In some embodiments, the distally and proximally directed barbs 108 could further engage, sever, and remove tissue as the device is twisted or rotated (along the axis of the device). In another embodiment, as shown in FIGS. 5A-B, one or more barbs 108 can be arranged so as to extend in a generally outward direction perpendicular to the outer surface 106. In this embodiment, the barbs 108 could engage, sever, and remove tissue as the device is twisted or rotated along its axis and/or as the device is moved in a proximal and/or distal direction. All of the barbs can be provided on the device extending in a uniform direction, or combinations of distally, proximally, and/or perpendicularly directed barbs 108 can be provided.

In one embodiment, for example, as shown in FIGS. 3A-D, the elongated member 101 is generally tubular, and a plurality of barbs 108 are situated about the outer circumference of the elongated member 101. In this embodiment, tissue can be severed and collected along a single or multiple tissue sampling surfaces. For example, the barbs 108 could engage and sever tissue from a tissue sampling site that surrounds the tubular member. For example, if the elongated member 101 is inserted through the mouth to collect tissue along the throat, the outer surface 106 could be sized and shaped such that the extended barbs 108 engage and sever tissue about the circumference or at multiple sides of the elongated member 101 as it is passed through the throat. In another embodiment, wherein the elongated member 101 is adapted to enter a tissue site (e.g. an organ) either by piercing and entering the tissue site or entering the tissue site through an incision (e.g. similar to a needle biopsy), the elongated member 101 becomes surrounded by the tissue, and the barbs 108 positioned about the circumference of the elongated member 101 engage and sever the surrounding tissue as the elongated member is moved within the tissue. Positioning the barbs 108 about the circumference of the elongated member 101 can also be useful in collecting tissue from a tissue collection site that does not surround the elongated member 101. For example, a first section of barbs 108 along one portion or side of the elongated member 101 could be positioned to collect tissue from the surface of a tissue collection site (e.g. from the surface of an organ). After the first section of barbs 108 collect tissue, the device could be rotated so as to position another section of barbs 108 near the tissue collection site for tissue collection. The device could be rotated or positioned until adequate tissue sampling is accomplished using various sections of barbs 108. In another embodiment, a plurality of barbs 108 can be located on a portion of the circumference or perimeter of the elongated member 101. In this embodiment, tissue can be severed and collected along a single tissue sampling surface, or multiple tissue sampling surface. For example, the elongated member 101 can be positioned with barbs 108 positioned near the tissue sampling surface and the barbs moved against the sampling surface. One or more additional tissue sampling surface(s) can further be accessed by barbs 108 simply by rotating or repositioning the elongated member such that the barbs 108 are positioned near the additional tissue sampling surface(s).

Any arrangement of barbs 108 along the elongated member 101 can be used. For example, rows of barbs 108 or random arrangements of barbs scattered about the elongated member 101 can be used.

In one embodiment shown in FIGS. 1A-5B, a plurality barbs 108 are provided along a given radius or cross section of the elongated member 101. For example, in one embodiment as shown in FIG. 3C, four barbs 108 are provided along a cross section of the elongated member 101. The barbs 108 are shown positioned equidistance from each other. A plurality of barbs can be situated along one or more cross sections, so as to allow for convenient and efficient tissue sampling along one or more tissue sampling surfaces. In one embodiment, the sampling portion 110 includes barbs 108 situated along one or more cross sections of the elongate member. For example, two, three, or four barbs 108 could be situated along one or more cross section. In some embodiments, more than four barbs 108 may be located along a given cross section. In other embodiments, fewer than four barbs 108 may be located along a given cross section. The barbs 108 along each cross section can be positioned equidistance from each other or can be more concentrated in some areas and less concentrated in others if desired. The distance between each cross section of barbs can be uniform or some cross sections having barbs can be positioned closer together than other cross sections of barbs along the elongated member 101.

In another embodiment, a plurality of barbs 108 are positioned in a random or scattered configuration along the elongated member 101.

The length of the portion of the elongated member 101 that has barbs 108 located thereon can vary. In some embodiments, barbs 108 are disposed along the elongated member 101 at various locations from the proximal to distal end of the elongated member 101. In other embodiments, barbs 108 are localized along a sampling portion 110 of the elongated member 101. The device can be adaptable for use in any type of biopsy procedure at any biopsy site and, thus, barbs can be suitably arranged.

In some embodiments, the sampling portion 110 dimensions are specifically provided based on the biopsy site and/or the amount of tissue sample desired. Such dimensions can be readily determined by one of skill in the art based on tissue sample site, barb 108 configuration, and the desired amount of tissue collection. For example, in one embodiment, the sampling portion 110 is adapted for use in obtaining a throat biopsy and can have a length ranging from about 5 mm to about 20 mm, and in some embodiments from about 10 mm to about 15 mm.

The size, shape and angle of projection of each barb 108 can vary, and the design of the barbs 108 can depend on factors such as biopsy site, type of tissue sampled, and size of tissue sample desired. Generally, the barbs angle away from the elongated member 101 so as to provides a barb height suitable to engage, sever, and remove an adequate tissue sample, but not so high that engagement, severing, and removal of tissue will result in excessive bleeding. Further, in some embodiments, it is desirable to obtain a particular layer or particular layers of tissue from a site and, thus, the height of the barb can be readily determined so as to engage, sever and remove the desired layer(s) of tissue from the site. Thus, for example, if it is desired to obtain four layers of tissue from a tissue site, and the barbs are sized too small, fewer than the four layers may be obtained.

In one embodiment, the barbs 108 are at least 0.5 mm long and no more than 10 mm long. In another embodiment, the barb length ranges from about 2 mm to about 6 mm. In another embodiment, the barb length ranges from about 5 mm to about 6 mm. In an embodiment, the height of the barbs as measured perpendicular from the outer surface of the elongated member 101 ranges from about 0.25 mm to about 5 mm. In another embodiment, the height of the barbs as measured perpendicular from the outer surface of the elongated member 101 ranges from about 0.5 mm to about 2 mm.

The barbs 108 are generally shown as having a pointed tip to facilitate tissue severing and removal. However, the barbs 108 are not limited to this profile, but, rather, are generally provided in a manner that allows for the severing and removal of tissue. For example, the tip could be slightly rounded or squared off and, if provided with adequate sharpness, would suitably possess the severing and removal properties for tissue sampling.

In one embodiment, the sampling portion 110 is approximately 13-15 mm in length and contains sections of barbs 108, each section of barbs positioned along a cross section of the elongated member 101. The barbs are 108 spaced approximately equidistant from each other along each cross section. Each barb 108 is approximately 2-6 mm in length, and, when in a deployed position away from the outer surface of the elongated member, is approximately 0.52 mm high. Each cross section of barbs is spaced from an adjacent cross section of barbs by about 0.5 mm to about 2 mm. In one embodiment, each cross section of barbs is spaced from an adjacent cross section of barbs by approximately 1 mm. These dimensions are given for illustrative purposes only and are not meant to be limiting.

In some embodiments, the device is provided with a plurality of interchangeable elongated members 101 adapted for different types of biopsy procedures. As such, for example, the interchangeable elongated members can be provided in different materials (e.g. with different flexibility/rigidity) and with different lengths, widths and geometries, and the barbs 108 can be provided in different shapes, sizes, numbers and/or at different locations. In other embodiments, the device can be provided with an elongated member 101 having a plurality of interchangeable sampling portions 110 adapted for different types of biopsy procedures. Thus, for example, the interchangeable sampling portions 110 can be provided in different materials (e.g. with different flexibility/rigidity) and with different lengths, widths and geometries, and the barbs 108 can be provided in different shapes, sizes, numbers and/or at different locations for each sampling portion 110. Any conventional interconnection means can be used to removably attach the elongated member 101 and sampling portions 110. The use of interchangeable elongated members 101 and/or sampling portions 110, can provide an adjustable device that suits the particular needs of various biopsy procedures.

Figure 3A:
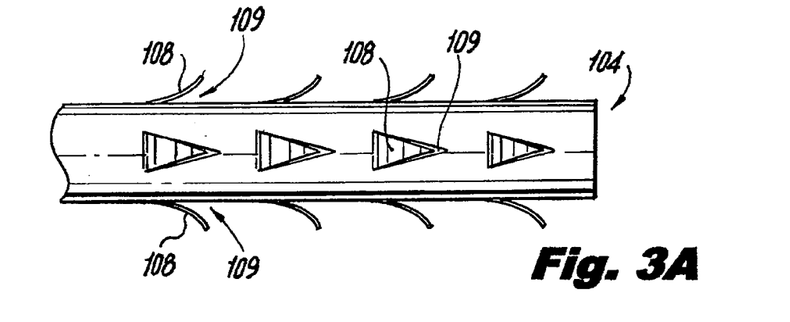
FIG. 3A shows a detailed view of barbs in accordance with one embodiment.
Figures 4A, 4B:
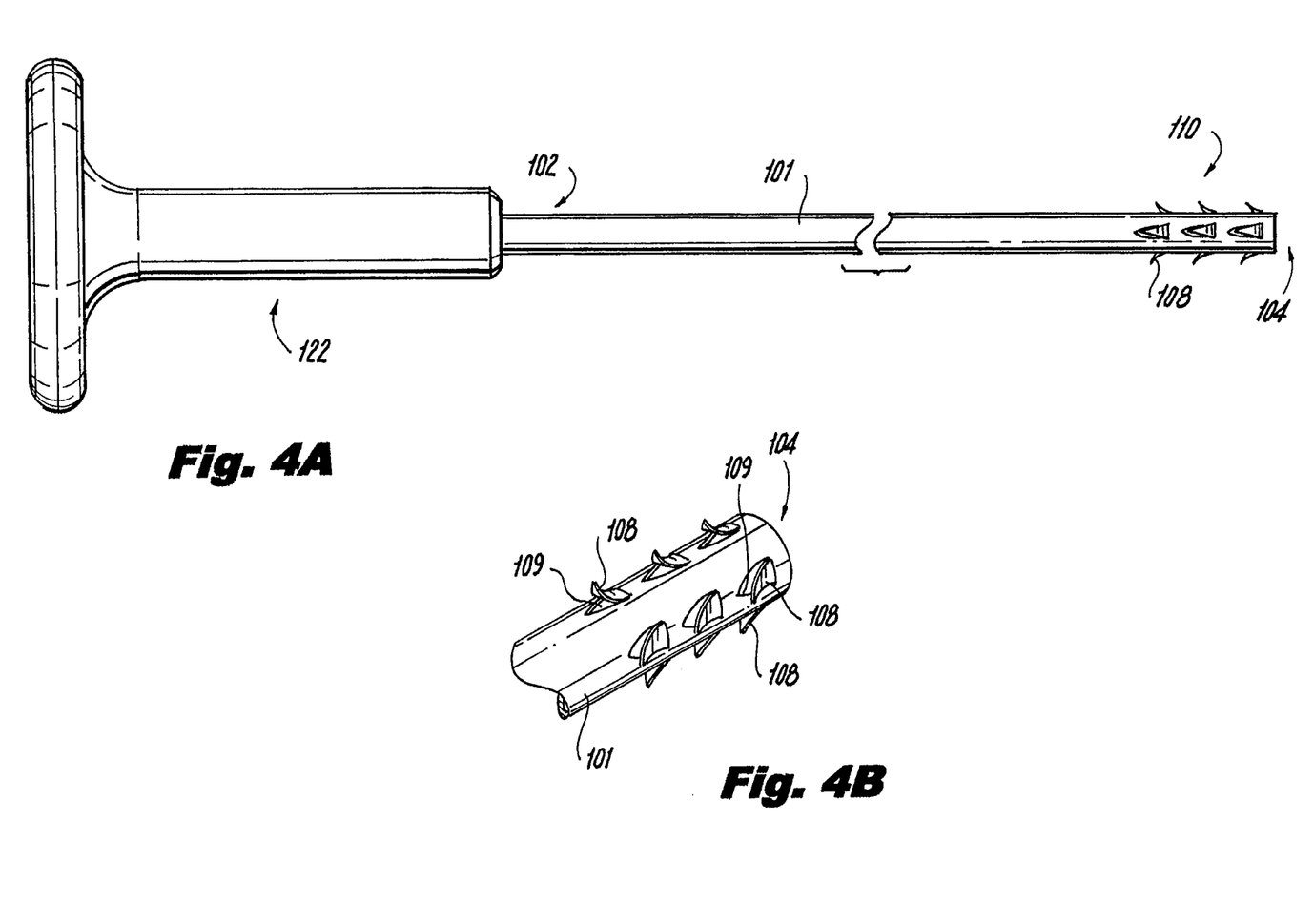
FIG. 4A shows a side view of an embodiment of the tissue sampling device, wherein the barbs are disposed in a proximal direction.
FIG. 4B shows a detailed side view of the sampling portion of FIG. 4A.
Figures 5A, 5B:
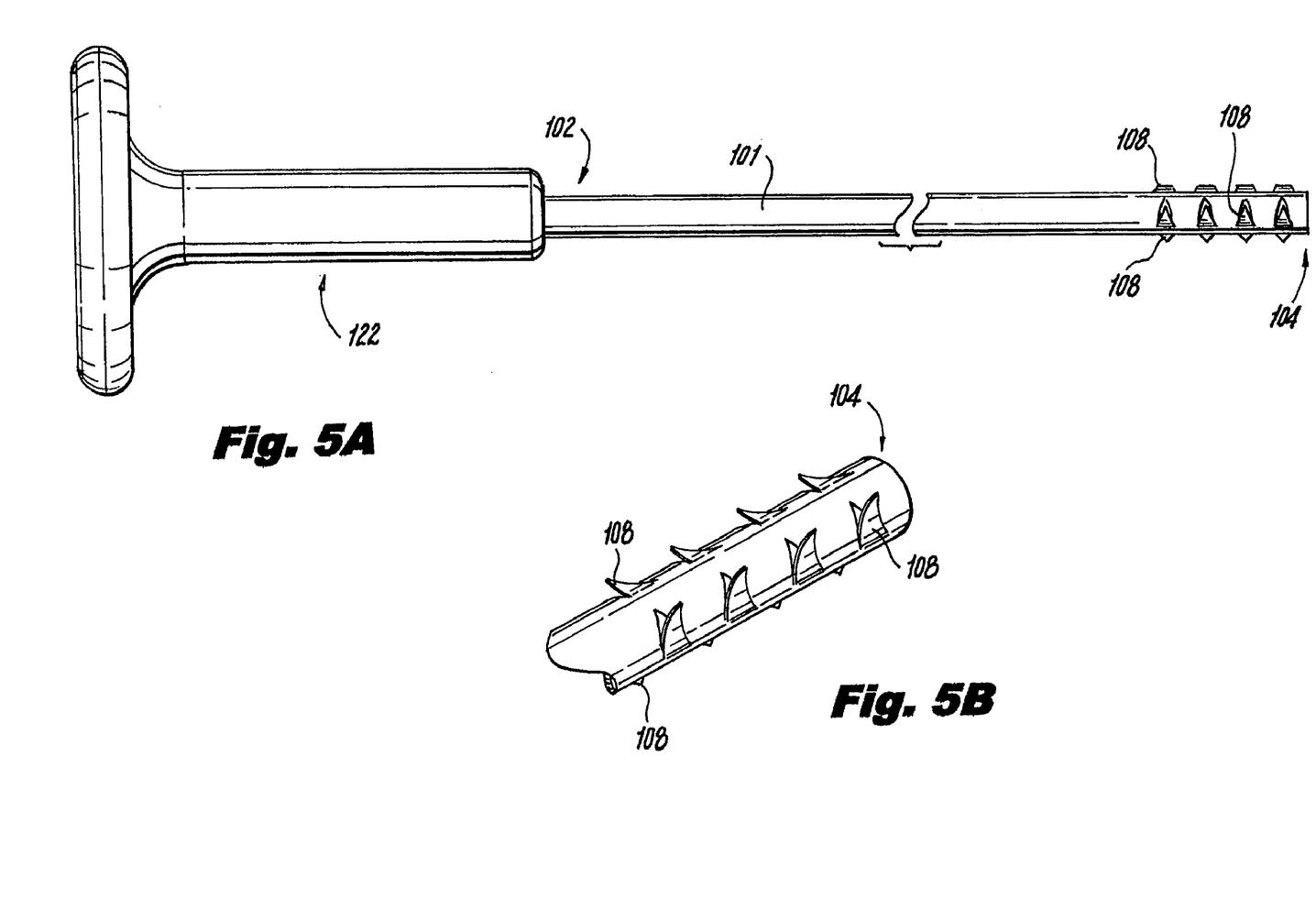
FIG. 5A shows a side view of an embodiment of the tissue sampling device, wherein the barbs are disposed perpendicular to outer surface of tubular member.
FIG. 5B shows a detailed side view of the sampling portion of FIG. 4A.

As shown, for example in FIGS. 3A and 4B, the barbs 108 can extend away from the outer surface 106 so as to define a space 109 between the barbs 108 and the outer surface 106 in which a tissue sample can be contained, held, or directed. Thus, tissue that is engaged, severed, and removed by the barbs 108 can be held within or directed into space 109 for retrieval upon removal of the device from the body. The elongated member can 101 further defined a plurality of openings 112 within the elongated member 101. The plurality of openings can be situated adjacent one or more barbs 108. The openings 112 are configured such that, as the tissue is severed and removed by barbs 108, the tissue passes into the openings 112 and is held within openings 112 for later retrieval. In some embodiments, the elongated member 101 is hollow or includes one or more lumen or channels (not shown) in connection with openings 112 such that the tissue passing into openings 112 can further enter the elongated member 101. As the tissue passes into openings 112, tissue exits space 109 and allows for additional sample collection, if desired.

In some embodiments, as shown in FIGS. 1B-D, 2A-2C, 3B, and 3C, the device can further include a coaxial sheath 114 that receives the elongated member 101. For example, the elongated member 101 can be slidably received within the coaxial sheath 114. Thus, the elongated member 101, including the sampling portion 110/barbs 108 can be withdrawn within or extended outside of sheath 114. In some embodiments, when the device enters the body, the sampling portion 110/barbs 108 are housed within the sheath 114. This can prevent inadvertent tissue sampling as the device is directed to the biopsy site. Once the device is at or near the biopsy site, the elongated member 101 can be advanced out of the sheath 114 with the sampling portion 110/barbs 108 exposed to obtain the tissue sample. After the sample is collected, the sampling portion 110/barbs can be retracted back inside of sheath 106, if desired.

In some embodiments, when the sampling portion 110 is housed within the sheath 114, the barbs 108 are pushed against or towards the outer surface 106 in a retracted position and, upon advancement out of the sheath 114, the barbs 108 return to a deployed state extending away from the outer surface 106. For example, in one embodiment, the sheath 114, elongated member 101, and barbs 108 are fabricated such that, as the barbs 108 are received in sheath 114, the inner surface of the sheath 114 engages the barbs 108 and presses the barbs 108 towards the outer surface 106 of the elongated member 101 in a retracted state. In one embodiment, the inner diameter of the sheath 114 is less than that of the sampling portion 110 plus deployed barbs 108 such that withdrawal of the barbs 108 inside of sheath 114 causes the inner surface of the sheath 114 to press the barbs 108 towards the outer surface 106 of the elongated member 101. The barbs 108 can be designed with sufficient flexibility such that they can be pressed towards the outer surface 106 repeatedly and, upon removal of pressure, they can return to a deployed state extending away from the outer surface 106. For example, the barbs 108 may be fabricated of an elastic material, such as an elastic stainless steel, Nitinol™ (an alloy of nickel and titanium) or the like, that will allow for both the deployed and retracted states.

In one embodiment, the elongated member 101 is hollow or includes one or more channels or lumen (not shown) in connection with the one or more openings 112. After tissue sample is collected, the sampling portion 110 can be pulled inside of sheath 114 or the sheath 114 advanced over the sampling portion 110, thereby pressing the barbs 108 against the outer surface 106. As the barbs 108 are pressed against the outer surface 106, the sample can be pushed or directed through openings 112 into the elongated member 101. The sampling portion 110 can subsequently be advanced outside of sheath 114, if desired.

In another embodiment, the device can include a deployment/retraction mechanism (not shown) that moves barbs 108 between a deployed state (extending away from the outer surface 106) and a retracted state (pushed against or towards the outer surface 106). For example, the barbs 108 can be held against the surface of sampling portion 110 with one or more tabs (not shown) or similar extensions that extend over the barbs 108 and are movable over the barbs 108 (to thereby retract barbs) and away from barbs 108 (to thereby deploy barbs).

Figure 2A:
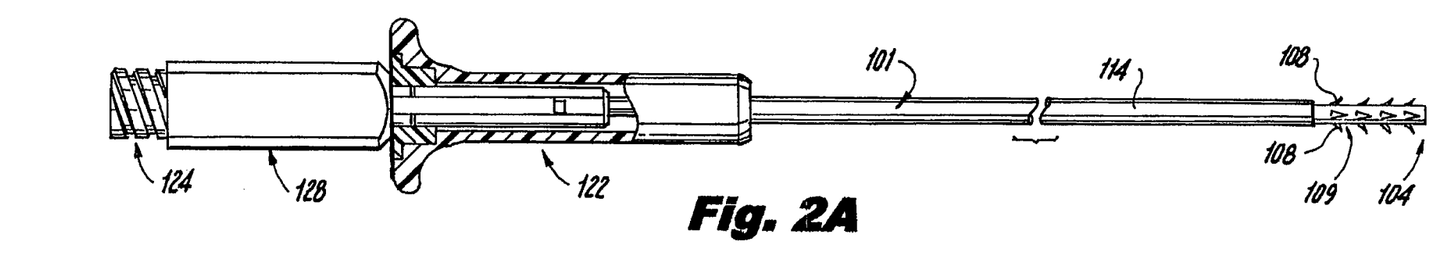
FIG. 2A shows a cut-away view of one embodiment of the tissue sampling device.
Figure 2B:
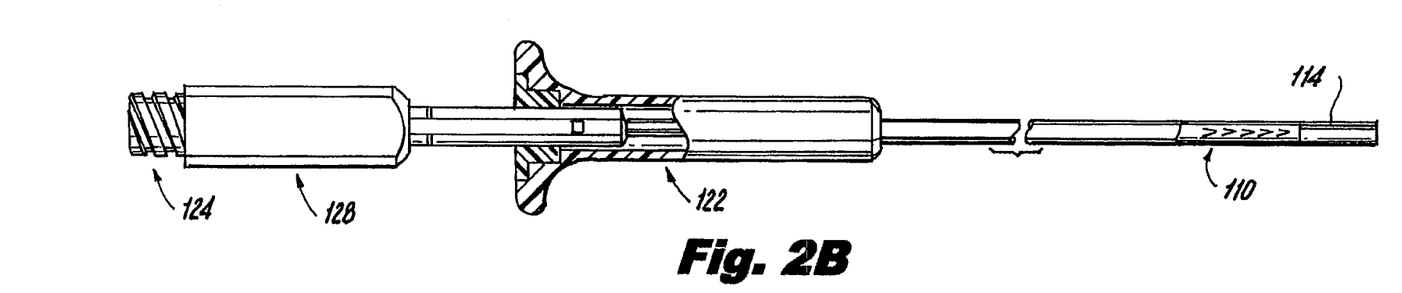
FIG. 2B shows a cut-away of the device in FIG. 2A, with a coaxial sheath housing elongated member.
Figure 2C:
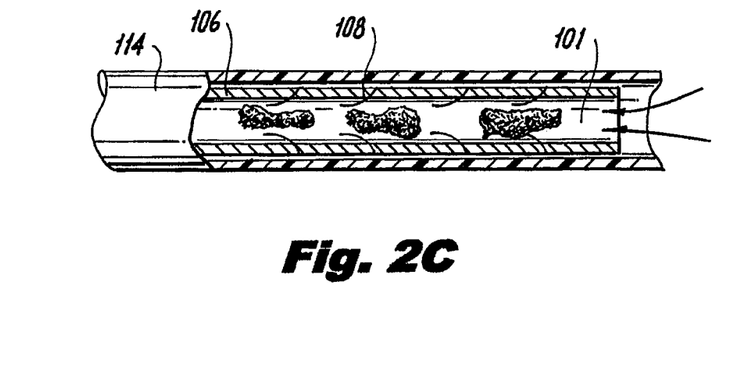
FIG. 2C shows a detailed cut-away view of a sampling portion of the elongated member of the device of FIGS. 2A and 2B when the sampling portion is housed within the sheath.
Figure 2D:
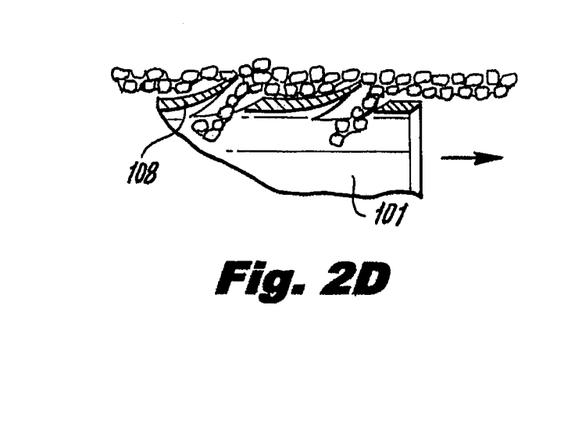
FIG. 2D shows a detailed view of the barbs engaging, severing, and removing tissue from a site.
Figures 3B, 3C, 3D:
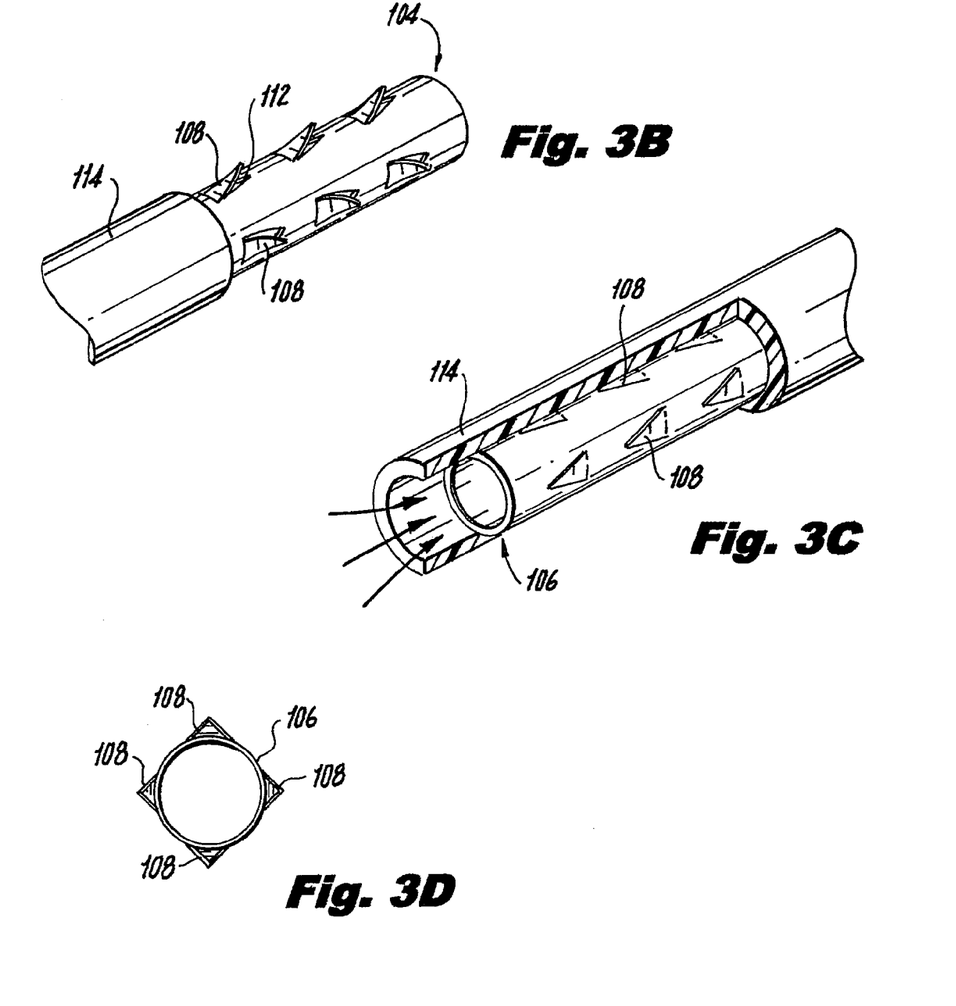
FIG. 3B shows a detailed perspective view of a tissue sampling portion in a deployed position outside of coaxial sheath.
FIG. 3C shows a detailed perspective view of a tissue sampling portion in a withdrawn position inside of coaxial sheath.
FIG. 3D shows a cross-sectional view of sampling portion.

In one embodiment, as shown in FIGS. 1B-D and 2A-2B the device includes a coaxial sheath 114 fixedly connected to the hand piece 122 as shown in FIGS. 2A-2B. The hand piece 122 and coaxial sheath 114 can include a channel 126 in which the elongated member 101 is slidably disposed. Movement of the hand piece 122 in a distal direction moves the coaxial sheath 114 distally over the elongated member 101 so as to house sampling portion 110 within the coaxial sheath 114. Movement of the hand piece 122 in a proximal direction moves the coaxial sheath 114 proximally relative to elongated member 101 so as to deploy the sampling portion 110 outside the coaxial sheath 114. In some embodiments, the elongated member 101 includes an distal end piece 128 that can be grasped by a user. Movement of distal end piece 128 and/or hand piece 122 relative to each other moves the elongated member 101 and/or coaxial sheath 114 relative to each other so as to retract and deploy the sampling portion 110 inside and outside of coaxial sheath 114.

The device can further include a locking mechanism (not shown) that can be activated to lock the elongated member 101, coaxial sheath 114, hand piece 122, and distal end piece 128 in place relative to each other. Thus, for example, the hand piece 122 can be moved in a distal direction over elongated member 101 until sampling portion 110 is housed within coaxial sheath 114. This position can be fixed by activating locking mechanism. To reposition the hand piece 122, elongated member 101, and coaxial sheath 114 relative to one another, for example, to deploy sampling portion 110 outside of coaxial sheath 114, the locking mechanism can be unlocked. The deployed position of the sampling portion 110 can further be fixed using a locking mechanism. Any conventional locking mechanisms that can be locked and unlocked repeatedly (e.g. mating tabs positioned on the coaxial sheath 114, elongated member 101, and/or hand piece 122) can be used.

The biopsy device can be in connection with an aspiration device to allow for aspiration of the tissue samples from the barbs 108 through elongated member 101. This aspect advantageously allows for collection of multiple tissue samples without withdrawal and reinsertion of the device from the sampling site.

FIGS. 2A-2C show an embodiment of an aspiration biopsy device in accordance with the present invention. As shown, the elongated member 101 is hollow and can be in connection with an aspiration mechanism. In other embodiments, the elongated member 101 can include one or more channels or lumen. The elongated member 101 can be in connection with any conventional aspiration mechanism, such as an aspiration syringe.

In one embodiment, the proximal end 102 of the elongated member 101 can be in connection with an end piece 128, which can, in turn, be in connection with an aspiration mechanism, for example, via a luer connector 124. In other embodiments, for example, as shown in FIGS. 1A, 4A and 5A, the elongated member 101 can be in connection with a hand piece 122 which can, in turn, be in connection with an aspiration mechanism. One or more openings 112 located adjacent barbs 108 can be situated such that severed and removed tissue passes into or towards the openings 112. Activation of the aspiration mechanism can pull the tissue through the openings 112 into elongated member 101.

In some embodiments, the device includes a coaxial sheath 114 or a retraction/deployment mechanism as set forth herein. Prior to aspiration, the sampling portion 110 can be retracted within coaxial sheath 114 or the retraction/deployment mechanism activated to retract barbs 108 against or towards the outer surface 106 prior to aspiration.

The various parts of the device can be fabricated of conventional materials used in forming surgical instruments, for example, surgical grade stainless steel, anodized aluminum, and polymeric materials and composites. The devices can be reusable and easily cleaned, and sterilized. In one embodiment, the various components can be at least partially disassembled for ease in cleaning and sterilizing. In other embodiments, all or portions of the devices are disposable.

The elongated member 101 is fabricated from any material that is known to those skilled in the art for use in fabricating surgical instruments. In certain embodiments, the elongated member is fabricated of a material that is lightweight and strong. The materials forming the elongated member 101 are generally bio-compatible materials, which include, but are not limited to, surgical grade stainless steel (e.g. 400 series stainless), anodized aluminum, Nitinol™ (an alloy of nickel and titanium), and polymeric materials and composites (e.g. nylon, HDPE and nano-clays). In some embodiments, the elongated member 101 is relatively rigid along its length and, suitably, could be fabricated of rigid materials and/or materials formed with a suitable thickness that will provide the desired rigidity. In other embodiments, for example, wherein the device travels along a torturous pathway and, thus, bending and flexibility is useful to facilitate the traversal of such a pathway, the elongated member 101 can be fabricated of materials that will provide the desired flexibility. Various thickness and dimensions of materials can also be used to provide the desired flexibility. In general, greater thickness will provide greater rigidity than a smaller thickness for the same or similar materials.

The dimensions of the elongated member 101 can vary depending on the type of biopsy performed and the type of access provided and can be readily determined by one of skill in the art. In one embodiment, the dimensions of the elongated member 101 are provided to contribute, at least in part, to the desired flexibility or rigidity of the device. Thus, at least a portion of the elongated member 101 can be designed with a diameter and/or wall thickness that will provide the desired flexibility or rigidity along that portion of the elongated member 101.

In one embodiment, the device is adapted for use in obtaining a throat biopsy by insertion through the patient's mouth to the throat biopsy site. The diameter of those portions of the elongated member 101 that are inserted through the mouth and throat are suitably sized for comfortable insertion based on the dimensions of the average human, or other mammal, throat. The diameter of the sampling portion 110 with deployed barbs 108 could be sized such that the barbs 108 engage, sever, and remove tissue sample along the throat about the perimeter of the sampling portion 110 as the sampling portion is moved within the throat.

In another embodiment, the device is adapted for delivery into the body through the channel of an endoscope (e.g., gastroscope, sigmoidoscope, or colonoscope). Typical endoscopes have a length ranging from about 100-250 cm and a channel diameter of approximately 2.0-3.8 mm. As such, the portion(s) of the device that enter through the endoscope have a length greater than the length of the endoscope such that the sampling portion 110 extends through and out of the endoscope into the biopsy collection site. The diameter of the portion(s) of the device that enter through the endoscope are less than the inner diameter of the endoscope and allows for manipulation of the device through and out of the endoscope. Such dimensions can be determined by one of skill in the art based on the geometry of the endoscope.

In another embodiment, the device is in the form of a fine needle biopsy device. The fine needle biopsy device can be in the form of a fine needle aspiration device. In this embodiment, the basic general features, (e.g. dimensions, geometry, etc.) of the device can be in accordance with conventional fine needle biopsy devices. In one embodiment, the elongated member 101 is in the form of a fine needle (e.g. 22 or 25 gauge) having sampling portion(s) 110, including barbs 108 located thereon as discussed generally herein. In one embodiment, the distal end 104 of elongated member 101 is sharpened so as to provide an entry point into the skin and into the tissue site. For example, the sharpened distal end 104 can, thus, pierce an organ for insertion of the elongated member 101 into the organ. Barbs 108 then engage, sever, and remove tissue sample. If in connection with an aspiration mechanism, the tissue sample is suctioned out from barbs 108 through elongated member 101 and additional tissue sample can be removed as desired. In another embodiment, the device includes a coaxial sheath 114 as described herein, which receives elongated member 101. In this embodiment, the coaxial sheath 114 can include a sharpened distal end to provide an entry point into the tissue site. Thus, for example, the elongated member 101 and barbs 108 can be housed within the coaxial sheath 114 as the coaxial sheath 114 pierces, for example, and organ. The elongated member 101 can subsequently be advanced through coaxial sheath 114 to the tissue collection site and tissue removed and collected. The elongated member 101 can be retracted within coaxial sheath 114 upon completion of the sampling procedure and the device withdrawn from the collection site.

In another embodiment, the device is in the form of a core needle biopsy device. In this embodiment, the basic general features, (e.g. dimensions, geometry, etc.) of the device can be in accordance with conventional core needle biopsy devices. In one embodiment, the device includes a elongated member 101 having sampling portion(s) 110, including barbs 108 located thereon as discussed generally herein. The elongated member 101 can have a sharpened distal end 104 to assist in inserting the device through the skin and into the tissue site as described with relation to the fine needle biopsy device. In another embodiment, the device can include a coaxial sheath 114 in which the elongated member 101 is received as described with relation to the fine needle biopsy device. The general use of the core biopsy device is similar to that described with relation to the fine needle biopsy device. The core needle biopsy device, like the fine needle biopsy device, can be used with aspiration.

Methods of forming the present devices can include molding processes, wherein the various parts are machined and molded into their desired shape. In some embodiments, the barbs 108 are fabricated from an elongated member by skiving or cutting the barbs 108 from the body of the elongated member. As or after the barbs 108 are skived or cut, they can be lifted up and away from the elongated member, thereby forming spaces 109. If the elongated member is hollow, and the barbs 108 are cut a full wall thickness of the elongated member, openings 112 are formed as the barbs 108 are lifted up and away from the elongate member. Openings 112 can also be formed and/or further shaped and sized after the barbs 108 are lifted up and away from a hollow elongated member. In some embodiments, the sharpness of the barbs 108 can be enhanced by various mechanical or manual sharpening methods or by chemical etch or similar procedures.

Methods of the present invention comprise obtaining a tissue sample from a desired body site using the device of the present invention.

In one embodiment, a method involves taking a biopsy from a patient's throat. The physician grasps the device, for example, by a hand piece 122 or a proximal end 102 of elongated member 101, inserts the elongated member 101 through the mouth, and advances the sampling portion 110 to the sampling site. The barbs 108 are then placed in contact with the sampling site and moved relative to the sampling site to engage, sever, and remove tissue. The device can be repositioned to obtain additional sample if desired.

In some embodiments, wherein the device includes a coaxial sheath 114, prior to inserting the elongated member 101 through the mouth, the barbs 108 can be withdrawn inside of coaxial sheath 114. The elongated member 101 can be locked into place using locking mechanism to prevent movement of barbs 108 outside of sheath 114 as the device is handled and the device advanced to the sampling site. Once the sampling portion 110 of the device is at or near the biopsy site, the barbs 108 are extended outside of sheath 114, first unlocking any locking mechanism. The elongated member 101 can then be locked into place with respect to sheath 114 to prevent inadvertent movement or withdrawal of sampling portion 101 110 back inside of sheath 114 as the device is manipulated.

After the barbs 108 engage, sever, and remove tissue, the device can be removed from the biopsy site and the tissue sample collected from space 109 and/or openings 112. In other embodiments, the device is connected to an aspiration mechanism and, after the barbs 108 engage, sever, and remove tissue, the aspiration mechanism is actuated to suction the tissue through the elongated member 101. Additional sample can then be collected, if desired. In another embodiment, the device is connected to an aspiration mechanism and, after the barbs 108 engage, sever, and remove tissue, the barbs 108 are withdrawn inside of sheath 114 and the tissue suctioned through elongated member 101 using an aspiration mechanism. In some embodiments, as the barbs 108 are withdrawn into sheath 114, the barbs 108 are directed towards the outer surface 106 so as to direct and/or push tissue into openings 112. The barbs 108 can then be extended outside of sheath 114 to collect additional tissue, if desired.

One skilled in the art will realize the invention may be embodied in other specific forms without departing from the spirit or essential characteristics thereof. The foregoing embodiments are therefore to be considered in all respects illustrative rather than limiting of the invention described herein.

The invention claimed is:

1. A method of obtaining a plurality of tissue samples from a site within a body of a patient, comprising:
    advancing a device configured to obtain the plurality of tissue samples to the site within the body of the patient, the device including a sheath and an elongated member having a tissue sampling portion, the elongated member defining an interior passage and a plurality of openings for receiving the plurality of tissue samples and being in communication with the interior passage, the tissue sampling portion including a plurality of barbs disposed about and extending from an outer surface of the elongated member in a uniform direction, the elongated member being slidably coupled to the sheath, the tissue sampling portion being in a housed position when the plurality of barbs are disposed inside of the sheath and being in a deployed position when the plurality of barbs are disposed outside of the sheath, the tissue sampling portion being in the housed position during the advancing;
    disposing the tissue sampling portion in the deployed position;
    after the disposing, severing and removing the plurality of tissue samples from the site within the body of the patient via at least two barbs from the plurality of barbs, the tissue sampling portion being rotated about an axis substantially parallel with a longitudinal axis of the elongated member to simultaneously sever and remove the plurality of tissue samples from the site within the body of the patient; and
    withdrawing the device from the site within the body of the patient.

2. The method of claim 1 wherein the method further comprises, after severing and removing the plurality of tissue samples from the site within the body of the patient, allowing the plurality of tissue samples to enter the interior passage through the openings.

3. The method of claim 2 further comprising providing aspiration through the elongated member to pull the plurality of tissue samples through the elongated member from the site within the body of the patient.

4. The method of claim 1 further comprising, after severing and removing the plurality of tissue samples from the site within the body of the patient, disposing the tissue sampling portion in the housed position.

5. The method of claim 4 further comprising, after disposing the tissue sampling portion in the housed position, providing aspiration through the elongated member to pull the plurality of tissue samples through the elongated member from the site within the body of the patient.

6. The method of claim 5 wherein the plurality of tissue samples is a first plurality of tissue samples, the method further comprising, after providing aspiration through the elongated member, disposing the elongated member in the deployed position, and severing and removing a second plurality of tissue samples from the site within the body of the patient with the at least two barbs.

7. A method of obtaining a plurality of tissue samples from a site within a body of a patient, comprising:
    advancing a device configured to obtain the plurality of tissue samples to the site within the body of the patient, the device including a sheath and an elongated member having a plurality of barbs disposed about and extending from an outer surface of the elongated member in a uniform direction, the elongated member defining an interior passage and a plurality of openings for receiving the plurality of tissue samples and being in communication with the interior passage, the sheath configured to cover the plurality of barbs during the advancing;
    sliding the sheath with respect to the elongated member such that at least two barbs from the plurality of barbs are disposed outside of the sheath;
    after the sliding, rotating the elongated member to simultaneously sever and remove the plurality of tissue samples from the site within the body of the patient via the at least two barbs from the plurality of barbs; and removing the device from the site within the body of the patient.

8. The method of claim 7, further comprising:

sliding the sheath with respect to the elongated member such that the sheath covers the plurality of barbs before removing the device from the site within the body of the patient.

9. The method of claim 7, wherein the severing and removing includes rotating the tissue sampling portion a single rotation about the axis substantially parallel with the longitudinal axis of the elongated member.

10. The method of claim 7, wherein the rotating includes rotating the elongated member a single rotation.

11. A method, comprising:

advancing a device to a site within a body of a patient, the device configured to obtain a plurality of tissue samples from the site within the body of the patient, the device including a sheath and an elongated member having a plurality of barbs disposed about and extending from an outer surface of the elongated member in a uniform direction, the plurality of barbs comprised of elastic materials and configured to move between a first position and a second position, the plurality of barbs being in the first position when the plurality of barbs are disposed within the sheath, the plurality of barbs being in the second position when at least two barbs from the plurality of barbs are disposed outside of the sheath, the plurality of barbs being in the first position during the advancing;

moving the plurality of barbs from the first position to the second position;

after the moving, severing and removing the plurality of tissue samples from the site within the body of the patient with the at least two barbs, the elongated member is moved relative to an axis substantially parallel with a longitudinal axis of the elongated member to sever and remove the plurality of tissue samples from the site within the body of the patient; and withdrawing the device from the site within the body of the patient.

12. The method of claim 11, wherein the moving includes sliding the sheath relative to the elongate member such that at least two barbs are disposed outside of the sheath.

13. The method of claim 11, wherein the severing and removing includes rotating the elongate member about the axis substantially parallel with the longitudinal axis of the elongated member to sever and remove the plurality of tissue samples from the site within the body of the patient.

* * * * *